(12) United States Patent
Rasulo et al.

(10) Patent No.: US 9,931,494 B2
(45) Date of Patent: Apr. 3, 2018

(54) STOMA-CREATING DEVICE

(71) Applicant: Cambridge University Hospitals NHS Foundation Trust, Cambridge (GB)

(72) Inventors: Frank Rasulo, Gussago (IT); Basil Matta, Cambridge (GB)

(73) Assignee: Cambridge University Hospitals NHS Foundation Trust, Cambridge (GB)

( * ) Notice: Subject to any disclaimer, the term of this patent is extended or adjusted under 35 U.S.C. 154(b) by 86 days.

(21) Appl. No.: 14/406,017

(22) PCT Filed: May 31, 2013

(86) PCT No.: PCT/GB2013/051450
§ 371 (c)(1),
(2) Date: Dec. 5, 2014

(87) PCT Pub. No.: WO2013/182841
PCT Pub. Date: Dec. 12, 2013

(65) Prior Publication Data
US 2015/0151093 A1    Jun. 4, 2015

(30) Foreign Application Priority Data

Jun. 7, 2012   (GB) .................................. 1210027.7

(51) Int. Cl.
*A61M 29/00* (2006.01)
*A61B 17/02* (2006.01)
(Continued)

(52) U.S. Cl.
CPC .......... *A61M 29/00* (2013.01); *A61B 17/0293* (2013.01); *A61B 17/3417* (2013.01);
(Continued)

(58) Field of Classification Search
CPC ..... A61M 29/00; A61B 17/0293; A61B 17/02
See application file for complete search history.

(56) References Cited

U.S. PATENT DOCUMENTS 3,759,263 A    9/1973 Taylor ...................... 128/207.29
4,130,113 A *  12/1978 Graham ............. A61B 17/0293
                                                  600/224
(Continued)

FOREIGN PATENT DOCUMENTS

FR    2825612    12/2002
GB    2365352     2/2002
(Continued)

OTHER PUBLICATIONS

International Search Report and Written Opinion dated Aug. 16, 2013 for International Application No. PCT/GB2013/051450, which was filed on May 31, 2013 and published as WO 2013/182841 on Dec. 12, 2013. (Inventor—Rasulo; Applicant—Cambridge University Hospitals NHS Foundation Trust) (pp. 1-12).
(Continued)

*Primary Examiner* — Ellen C Hammond
(74) *Attorney, Agent, or Firm* — Ballard Spahr LLP

(57) ABSTRACT

The invention provides a stoma-creating apparatus for creating a stoma in a subject. The apparatus comprises first and second members, and one or more dilation means provided on the first and/or second member. In use, upon respective movement of the first and second members, the stoma-creating apparatus is arranged to move between a first closed configuration in which the one or more dilation means is substantially closed, and a second open configuration in which the one or more dilation means is substantially dilated, thereby creating a stoma in the subject. The invention is particularly concerned with creating stomas which hold a tracheostomy tube in position on the trachea of a patient undergoing a tracheostomy, or for securing a valve or other medical device in position adjacent a patient's pneumothorax.

20 Claims, 4 Drawing Sheets

(51) Int. Cl.
*A61M 16/04* (2006.01)
*A61B 17/34* (2006.01)
*A61B 17/00* (2006.01)
*A61B 17/29* (2006.01)

(52) U.S. Cl.
CPC .............. *A61M 16/0472* (2013.01); *A61B 2017/00407* (2013.01); *A61B 2017/2936* (2013.01)

(56) References Cited

U.S. PATENT DOCUMENTS

| | | | | |
|---|---|---|---|---|
| 7,182,730 | B2* | 2/2007 | Fehling | A61B 1/32 |
| | | | | 600/210 |
| 2004/0103900 | A1 | 1/2004 | Melker | 128/207.29 |
| 2005/0203347 | A1 | 9/2005 | Fehling | 600/210 |
| 2007/0219416 | A1* | 9/2007 | Perez-Cruet | A61B 17/02 |
| | | | | 600/219 |
| 2010/0274094 | A1* | 10/2010 | Abdelgany | A61B 17/0293 |
| | | | | 600/207 |
| 2011/0301423 | A1* | 12/2011 | Koros | A61B 17/02 |
| | | | | 600/229 |

FOREIGN PATENT DOCUMENTS

| | | |
|---|---|---|
| GB | 2377383 | 1/2003 |
| WO | WO 2013/182841 | 12/2013 |

OTHER PUBLICATIONS

United Kingdom Intellectual Property Office Search Report dated Sep. 28, 2012 for Application No. GB 1210027.7. (pp. 1-6).

* cited by examiner

STOMA-CREATING DEVICE

CROSS-REFERENCE TO RELATED APPLICATIONS

This application is a U.S. National Phase Application of International Application No. PCT/GB2013/051450, filed on May 31, 2013, which claims priority to GB Patent Application No. 1210027.7, filed Jun. 7, 2012, each of which are hereby incorporated by reference in their entirety.

The present invention relates to stoma-creating devices for producing a stoma in a patient's body, and to their uses in methods for creating a stoma. The invention is particularly concerned with creating stomas which hold a tracheostomy tube in position on the trachea of a patient undergoing a tracheostomy, or for securing a valve or other medical device in position adjacent a patient's pneumothorax.

Tracheostomy procedures generally involve making an incision on the anterior aspect of the neck, and opening a direct airway through an incision in the trachea. The resulting stoma can serve independently as an airway, or as a site for the insertion of a tracheostomy tube, which allows a patient to breathe without the use of his or her nose or mouth. Both surgical and percutaneous techniques are widely used in current surgical practice.

There are several different methods for performing percutaneous dilational tracheostomy (PDT), the most common of which is Ciaglia, in which a guide wire is initially placed between the first and second, or the second and third tracheal rings, and a series of stiff plastic dilators are sequentially forced into the tracheal wall over the guide wire until a stoma of sufficient size to accommodate the desired traceostomy tube is created. A PDT is usually performed on an anaesthetised patient, and requires neck extension and a sterile field. While some clinicians continue to perform PDT blindly, some have adopted a technique of observing and directing needle placement to facilitate the positioning of the guide wire. However, a significant problem with using the Ciaglia technique is that the posterior wall of the trachea is damaged, and, in addition, the tracheal rings are often fractured during the procedure due to excessive force applied thereto.

The so-called "Blue Rhino" dilator is a single, tapered dilator that is used instead of the sequential dilators of Ciaglia, to form the stoma into which the tracheostomy tube is inserted. However, a substantial amount of force is needed to insert the dilator and tracheostomy tube, and this can result in the trachea collapsing, and the tracheal rings becoming fractured.

Another tracheostomy method involves the use of the Griggs forceps, which is a tracheal spreader that has been modified to thread over the guide wire, and involves forceps dilation to create the tracheal stoma. As with the Ciaglia technique, the trachea is inserted in between the appropriate tracheal rings. However, a problem with using the Griggs forceps is that force is placed on the joining tissue between the cartilage rings, and, as the forceps are open, there is a risk that the tissue will be torn in a non-uniform manner along the weakest part.

In addition to the above problems encountered with known tools and techniques for carrying out a tracheostomy procedure, additional disadvantages include the fact that they should be carried out by an experienced clinician, who must use both hands. Furthermore, currently, the clinician has to remove the device that is used to create the stoma before the tracheostomy tube itself can be fed into the stoma. A problem with this is that, when the initial device to create the stoma is removed from the patient, the stoma tends to close up, meaning that the clinician has to carefully prise it back open before the tracheostomy tube can be inserted. Accordingly, there is a need in the art to provide an improved apparatus for facilitating tracheostomy procedures.

A pneumothorax is a collection of air or gas in the pleural cavity of the chest between the lung and the chest wall. It may occur spontaneously in people without chronic lung conditions ("primary"), as well as in those with lung disease ("secondary"), and many pneumothoraces occur after physical trauma to the chest, or as a complication of medical treatment. The symptoms of a pneumothorax are determined by the size of the air leak from the lungs, and the speed by which it occurs. They may include chest pain in most cases, and shortness of breath in many. In a small proportion, the pneumothorax leads to severe oxygen shortage and low blood pressure, progressing to cardiac arrest unless treated.

Small spontaneous pneumothoraces can correct themselves and require little or no treatment, especially in those with no underlying lung disease. However, in larger pneumothoraces, or when there are severe symptoms, the air has to be aspirated with a syringe, or a one-way chest tube is inserted to allow the air to escape. In order to carry out such correction procedures, a stoma must be first created at a position which corresponds with pneumothorax, and then an air-release tube is attached to the stoma, before the air can be aspirated. Therefore, there is a requirement for apparatus for releasing the air from a pneumothorax. In addition, once the pneumothorax has been successfully aspirated, it is then necessary to re-inflate the collapsed lung.

Common to all of the above-mentioned medical procedures is the requirement for the clinician to initially create a stoma in the patient's body (e.g. the trachea or chest etc), and then retain the thus created stoma (i.e. its shape and size) in order to allow the attachment of a medical device thereto, such as a conduit, for example a tracheostomy tube, valve or pump etc. Accordingly, the inventors have developed stoma-creating devices, which can be used in a tracheostomy procedure, or for aspirating a pneumothorax, or inflating lungs.

According to a first aspect of the present invention, there is provided a stoma-creating apparatus for creating a stoma in a subject, the apparatus comprising first and second members, and one or more dilation means provided on the first and/or second member, wherein, in use, upon respective movement of the first and second members, the stoma-creating apparatus is arranged to move between a first closed configuration in which the one or more dilation means is substantially closed, and a second open configuration in which the one or more dilation means is substantially dilated, thereby creating a stoma in the subject.

Advantageously, upon movement of the two members with respect to each other, the apparatus is capable of performing a very gradual and highly controlled dilation of the one or more dilation means in the subject (i.e. a patient), which ensures a uniform opening of the stoma, including skin and tracheal tissue, and this significantly reduces discomfort to the subject, and reduces the risk of post-procedure complications. Furthermore, with the apparatus of the invention, there is no need to use blind insertion of long dilators (as would be the case, for example using the known Blue Rhino device) into the trachea, which is associated with many complications, such as posterior tracheal wall perforation, anterior tracheal wall damage, and cartilage ring fracture. In addition, using the apparatus of the invention, there is no need to apply downward pressure on the anterior tracheal wall for dilation to occur. Also, the apparatus reduces the time taken to safely create a stoma by removing certain steps involved in prior art methods.

It will be appreciated that a stoma is an opening, either natural, or surgically created, which connects a portion of the body cavity to the outside environment. A medical device may be attached at least adjacent to, and preferably in, the stoma that is created. Suitable medical devices which may be attached may include a conduit along which gas or liquid may flow. For example, the medical device may be a tracheostomy tube, a valve, a pump or a fibrescope. Therefore, preferably the apparatus of the first aspect is a tracheostomy apparatus. A fibrescope is often used in order to guide the clinician during the initial phase, so as to be sure that only the trachea is being accessed, when conducting a tracheostomy.

Preferably, the first and second members of the apparatus rotatably engage with each other. The first and/or second member may comprise a ring-shaped body, which may be substantially planar. The first and/or second member may comprise a handle, which may extend away from the body, preferably a periphery thereof. The or each handle may extend at an angle with respect to the plane of the body to which it is attached, i.e. the handle and corresponding body are not coplanar. For example, the or each handle may extend away from the body at an angle of at least about 10°, 20° or 30° with respect to the plane of the body. Advantageously, as the handles are not coplanar with the bodies, they extend away from the subject when the apparatus is being used, thereby giving the user (e.g. the clinician) a much improved operating position.

Preferably, the bodies of the first and second members are rotatably attached to each other such that they are capable of moving between the open and closed configurations. Preferably, when the apparatus is in the closed configuration, the handles are spaced apart, as shown in FIG. 1, and when the apparatus is in the open configuration, the handles substantially align with one another.

Preferably, the one or more dilation means is arranged, in use, to engage with the subject when in the first closed configuration. The one or more dilation means is arranged, in use, to engage with the subject and dilate to form the stoma, as the apparatus is moved from the closed configuration into the open configuration. Preferably, the apparatus comprises at least two, three, or at least four dilation means.

The one or more dilation means may comprise a body section from which extends a blade. Preferably, the blade extends from at least adjacent one end of the body section. Preferably, the end of the body section from which the blade extends tapers inwardly. The blade preferably extends at an angle of between 70° and 110° with respect to the plane of the body section, more preferably at an angle of between 80° and 100° with respect to the plane of the body section, and preferably at an angle of between 85° and 95° with respect to the plane of the body section.

The length of the blade may be about 5-30 mm, or about 10-20 mm depending on the type, size and location of the stoma to be created and the size of the subject. The blade may be metallic. The blade may taper inwardly to a sharp point at its distal end in order to improve the ease of insertion into the subject, and to increase the strength at the proximal base of the blade. The distal end of the blade may be bevelled to a tip so that when the apparatus is in the first configuration, and the blades are brought together, adjacent tips meet to form a pointed end to further ease insertion into the subject.

An outer side of the blade may be substantially curved so as to form a cylindrical shape when adjacent blades are brought together when the apparatus is in the first configuration. This again assists their insertion into the subject, and also resembles the outer curved profile of a medical tube to be subsequently or simultaneously inserted into the stoma being created. An inner side of the blade may be bevelled to allow for a close fitting to an adjacent blade when the apparatus is in the first configuration. The blade, and preferably an inner side thereof, may comprise a groove, which extends in a substantially parallel direction with the respect to the elongate axis of the blade. Preferably, when the apparatus is in the first configuration, the grooves on adjacent blades collectively create a channel in which a guide wire can be accommodated.

The first member may comprise one or more guide slot, which is arranged to slidably receive the or each dilation means, and preferably the body section thereof. The or each guide slot is preferably provided in the body section of the first member. Preferably, the or each guide slot extends radially outwardly from an inner portion towards a periphery of the first member. Preferably, the or each guide slot is substantially linear, i.e. straight. The body section of the or each dilation means is preferably arranged, in use, to slide along its corresponding guide slot (preferably in either direction) as the apparatus is moved between the open and closed configurations.

The second member may comprise one or more guide slot, which is arranged to receive the or each dilation means, and preferably a protrusion or pin extending out of the body section of the or each dilation means. The or each guide slot is preferably provided in the body section of the second member. Preferably, the or each guide slot extends at an angle from an inner portion towards a periphery of the second member. Preferably, the or each guide slot is non-linear, i.e. curved or angled. The radial distance of an inner end of the or each guide slot is less than the radial distance of the opposite outer end of the slot. The pin of the or each dilation means is preferably arranged, in use, to slide along its corresponding guide slot (preferably in either direction) as the apparatus is moved between the open and closed configurations.

Preferably, in use, the apparatus is arranged to be moved from the first configuration to the second configuration, and urge the pin on the or each dilation means along the guide slot towards the periphery of the second member. Preferably, as the pin moves along its guide slot, the apparatus is arranged, in use, to urge the or each dilation means along the guide slot towards the periphery of the first member. Preferably, the or each dilation means radially expands as it is moved towards the second configuration. Conversely, the or each dilation means radially contracts as it is moved towards the first configuration. Advantageously, the angled guide slots in the second member serve to draw the dilation means outwards, while the straight guide slots ensure that the dilation means and their blades are moved in a lateral direction.

Preferably, the or each guide slot in the second member is longer than the or each guide slot in the first member. Advantageously, this extra length and the angled arrangement in the body provides a slow and gradual control of the motion of the dilation means along the slots as the stoma is created. Accordingly, the user can ensure that that the subject is not hurt by the blades radially expanding too quickly.

The guide slot provided in the second member may comprise one or more detent for receiving the pin extending out of the body section of the or each dilation means. For example, the detent may be provided at one or both ends of the guide slot in the second member, or at spaced apart positions along the guide slot. The detent provides friction and therefore a small amount of resistance to the position of the pin when the apparatus is either in the first or second configuration or at a point in between these two configurations.

The apparatus may comprise one or more ratchets, which are arranged, in use, to retain the apparatus in a fixed position at, or in between, the first and second configurations.

For example, a surface of the dilation means (and preferably the body section) may comprise a first ratchet which is operable to engage with a second ratchet provided on first or second member. Preferably, the second ratchet is provided in the guide slot in the first member. Advantageously, as the ratchets engage with each other at different positions therealong, the clinician can release the apparatus without the risk of the stoma inadvertently closing.

The apparatus preferably comprises dilation indication means for indicating to an operator the desired diameter of the stoma that has been created. The indication means ensures that the operator is aware of how far the dilation means (and especially the blades) blades have dilated, thus ensuring that the least amount of pressure is applied to produce the desired dilatation and so that there is no over-dilation. In one embodiment, the indication means may comprise a ratchet provided in the guide slot in the first member and a corresponding ratchet provided on the dilation means itself. In another embodiment, the indication means may comprise corresponding ratchets provided in the body and/or handle of the first and/or second member.

The apparatus may comprise a measurement guide which corresponds to the respective positions of the first and second members, and preferably of the two handles or the two bodies thereof. One of the members (preferably the body thereof) may be at least partially transparent to show the position of the dilation means therein. The measurement guide may be disposed on an upper handle, such that the size of stoma created would allow the operator to insert the correct size tube therein. The measurement guide may therefore indicate tracheostomy tube sizing or the diameter of the stoma created.

Clearly, the stoma-creating apparatus of the first aspect has utility for forming a stoma in a patient, for example a patient undergoing a tracheostomy or pneumothorax.

Hence, in a second aspect, there is provided a use of the stoma-creating apparatus of the first aspect for creating a stoma in a subject.

In a third aspect, there is provided a method of creating a stoma in a subject, the method comprising: (i) contacting a subject's body with one or more dilation means provided on a first member and/or a second member; and (ii) moving the first and second members with respect to each other, such that they move from a first configuration in which the one or more dilation means is substantially closed, and a second configuration in which the one or more dilation means is substantially dilated, thereby creating a stoma in the subject.

In order to create a stoma, the clinician first makes an incision in the subject's skin at the target site, for example on the trachea or the chest. The incision may be made with a hypodermic needle. Insertion of the needle may be carried out by fibre optic guidance in order to locate the trachea lumen. The needle may then be removed leaving the sheath in place and through which a guide wire may be inserted. It will be appreciated that, using traditional methods, the incision would have to be at least 2-3 cm in diameter. Then, along the guide wire, a dilator may be used to enlarge the incision creating an initial opening.

The stoma-creating device of the first aspect may then be urged towards the subject along the guide wire, which ensures that the stoma is formed at the correct position. The or each dilation means is preferably closed such that the grooves in each of the closed blades collectively create a channel through which the guidewire can extend. The apparatus is fed over and down the guidewire towards the subject, and the blades of the apparatus may then be inserted into the subject, for example the trachea between the cartilage rings. The handles may then be rotated with respect to each other and brought together. This rotational movement may cause the pins on the dilation means to be gradually urged outwardly along the angled guide slots towards the periphery of the second member. As the pins move along angled slots, each dilation means preferably radially expands outwardly along the linear guide slots, thereby forming the stoma. Once the desired retraction position has been achieved, the operator may remove the apparatus and insert a medical tube such as a tracheostomy tube (not shown) or other tube for fluid to pass along. The tracheostomy tube may be inserted into the stoma while the apparatus is in place retracting the stoma. Some tracheostomy tubes have a folding neck flange thus allowing the apparatus to be withdrawn over the tube.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which.

EXAMPLES

The inventors have developed a device 2, which is shown in the Figures, and associated methods for creating a stoma in the body of a patient. For example, the stoma may be required if a clinician wishes to carry out a tracheostomy, or needs to release trapped gas from a pneumothorax, or re-inflate a collapsed lung. Thus, the device 2 could be described as being a tracheostomy device etc.

Figure 1:
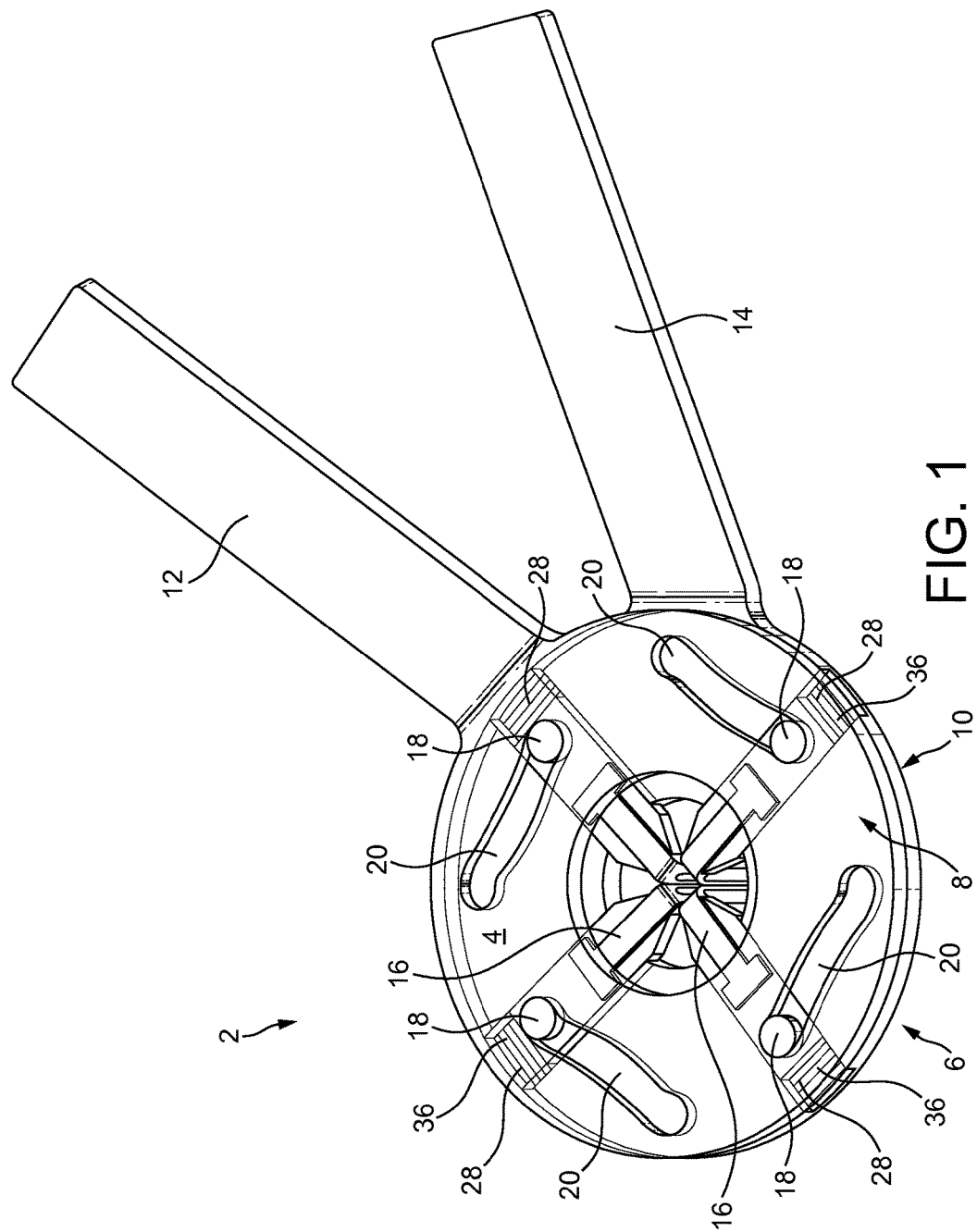
FIG. 1 shows a cross-sectional perspective view of an embodiment of a stoma creating device according to the invention that is used to create a stoma in a patient, such as a tracheostomy. The device includes four retractors which are shown in a closed configuration.

Referring to FIG. 1, the device 2 consists of an upper section 4 and a lower section 6, which are arranged to mutually engage with each other. Each section 4, 6 consists of a ring-shaped, substantially planar body 8, 10 which has an elongate handle 12, 14 extending from the circumference thereof. The handles 12, 14 extend away at an angle of about 30° with respect to the plane of the bodies 8, 10 and therefore from the patient when the device 2 is being used, in order to give the clinician an improved operating position.

Figure 2:
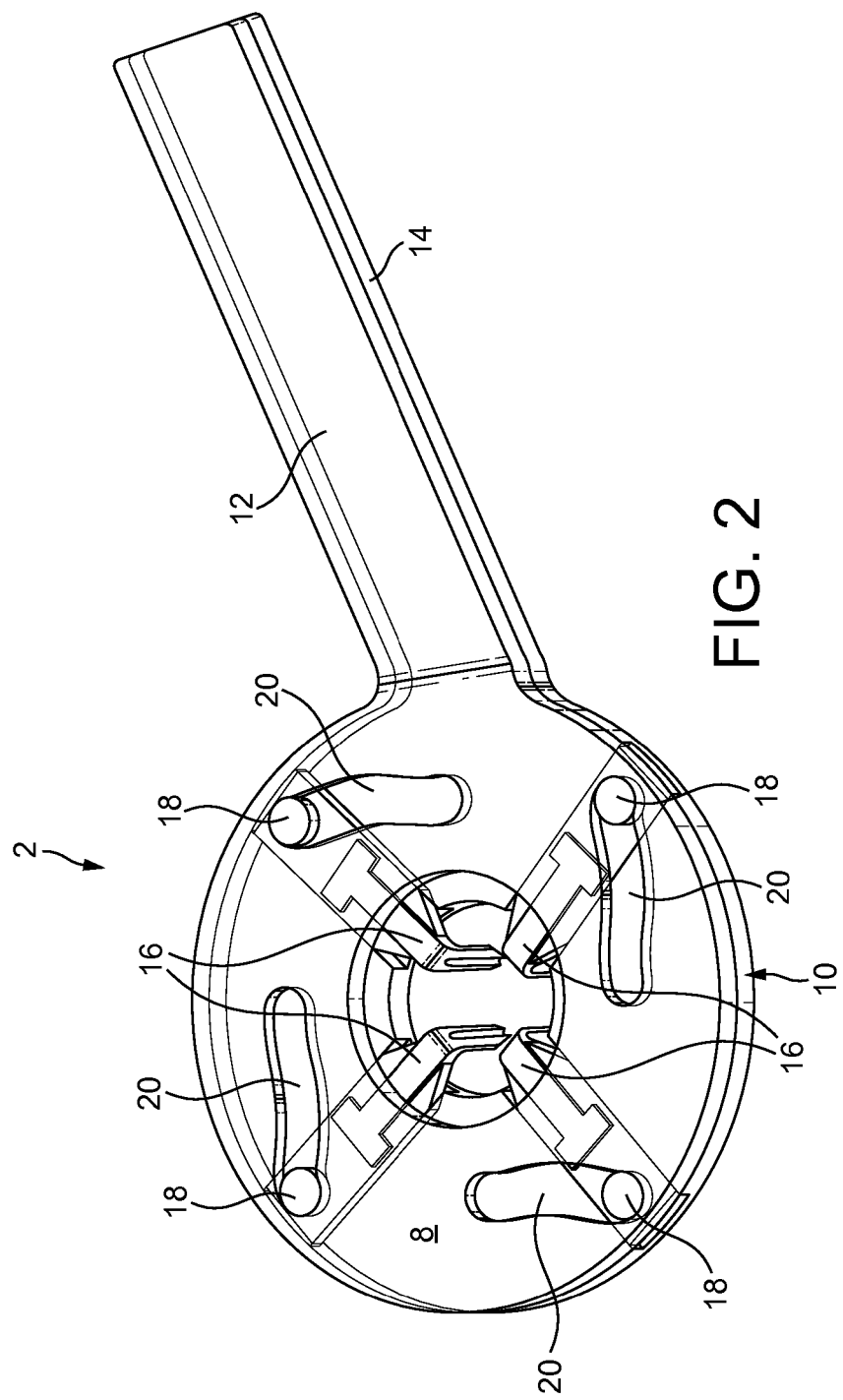
FIG. 2 shows a cross-sectional perspective view of the device shown in FIG. 1 in an open configuration with the retractors open.
Figure 3:
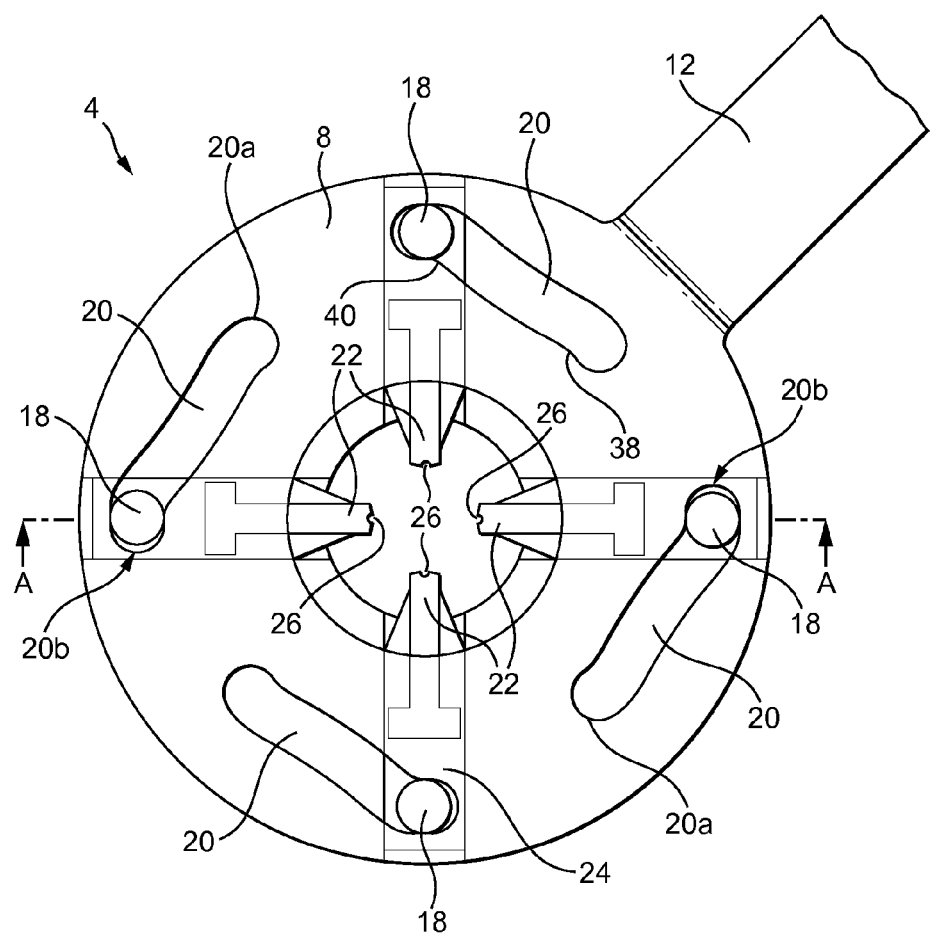
FIG. 3 shows an enlarged cross-sectional plan view from above of the device in the open configuration.
Figure 4:
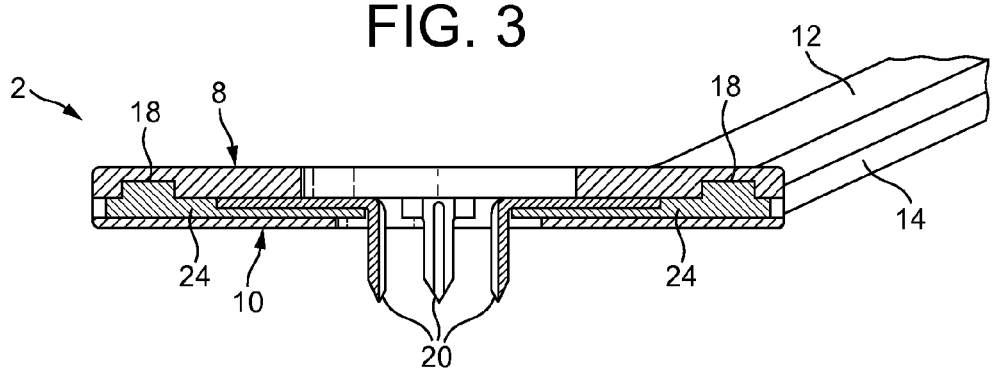
FIG. 4 shows an enlarged schematic side view of the device along axis A-A in FIG. 3 in the open configuration.
Figure 5:
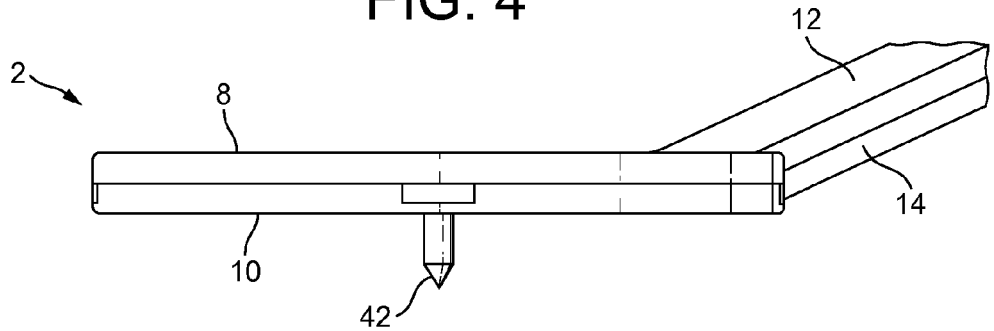
FIG. 5 shows an enlarged side view of the device shown in FIG. 1 in the closed configuration.

The two bodies 8, 10 of sections 4, 6 are rotatably attached to each other such that they can move between an open configuration (as shown in FIGS. 2, 3 and 4) and a closed configuration (as shown in FIGS. 1 and 5). When in the device 2 is closed configuration, the handles 12, 14 are spaced apart, as shown in FIG. 1, and when the device 2 is in the open configuration, the handles 12, 14 align with one another. The device 2 includes an arrangement of four retractors 16, which are designed to engage with a patient and dilate to form the stoma, as the device 2 is moved from the closed configuration (see FIG. 1) into the open configuration (see FIG. 2). However, it will be appreciated that fewer (i.e. 2 or 3) or more (i.e. 5 or 6) retractors could be provided and would give a similar result, as long as several areas of support are provided when forming the stoma, for example support would be needed for each tracheal ring being retracted during a tracheostomy.

Figure 6:
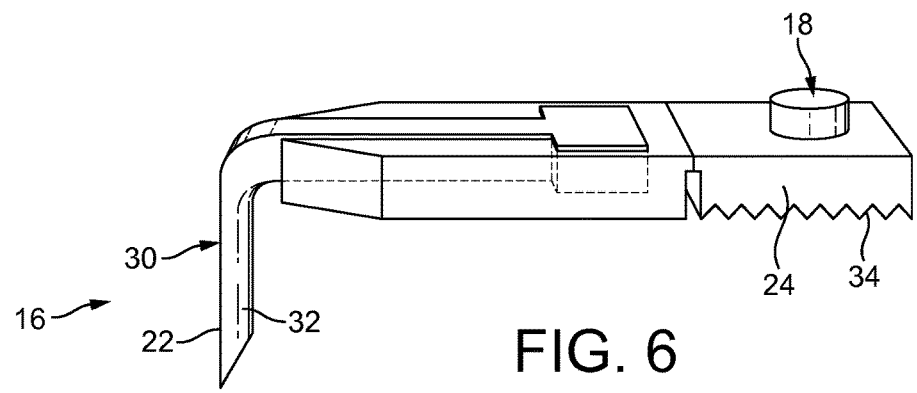
FIG. 6 shows a perspective side view of one of the device's retractors.
Figure 7:
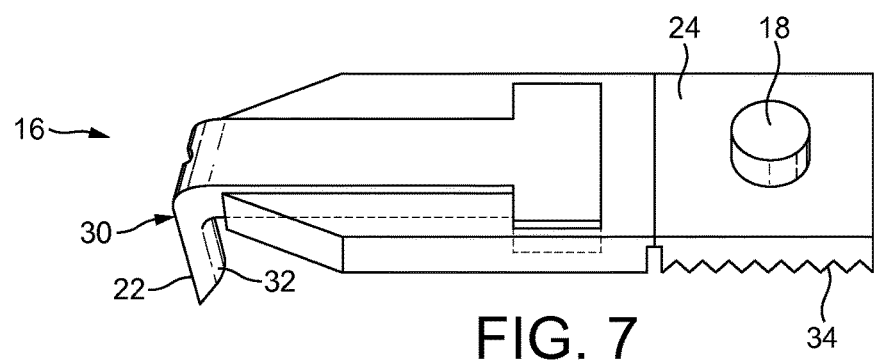
FIG. 7 shows a perspective view from above of the retractor.
Figure 8:
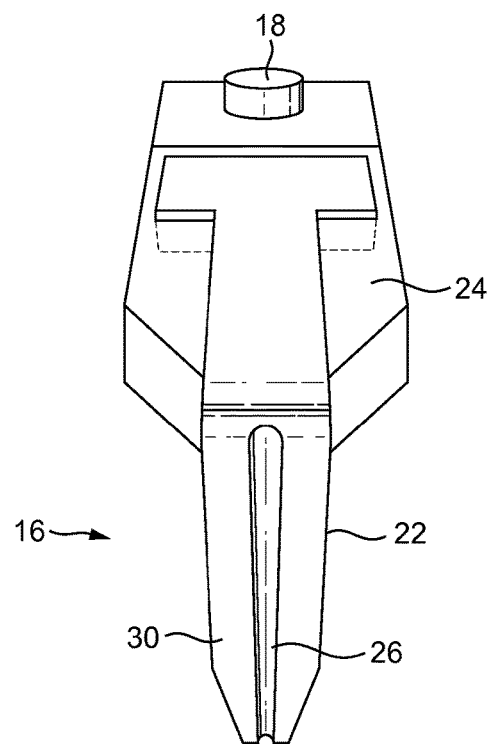
FIG. 8 shows a perspective front view of the retractor.

Referring now to FIGS. 6-8, there are shown various detailed views of one of the retractors 16, although it will be appreciated that the retractors 16 are all the same. As can be seen, each retractor 16 includes a block-shaped body section 24 (which can be made of plastic) from one end of which extends a thin metallic blade 22. The blade 22 is angled downwardly at an angle of about 90° with respect to the plane of the body 24. As can be seen in FIG. 7, one end of the body section 24 of the retractor 16 tapers inwardly to where it meets the blade 22 angled at 90°. The length of each blade is about 10 mm, although a length of about 15-20 mm could be used to create a stoma in patients with larger necks. The blade 22 tapers inwardly to a sharp point at its distal end in order to improve the ease of insertion into the patient, and to increase the strength at the proximal base of each blade 22. In addition, the distal end of the blade 22 is bevelled to a tip so that when all of the blades 22 are brought together, when the device is in the closed configuration as shown most clearly in FIG. 5, the tips meet to form a pointed end to ease insertion into the patient.

An outer side 32 of each blade 22 is curved so as to form a cylindrical shape when all four of the blades 22 are brought together, again to aid insertion into the patient, and to resemble the outer curved profile of a medical tube to be inserted into the stoma, for example a tracheostomy tube (not shown). In contrast, an inner side 30 of the blade 22 is bevelled to allow for a close fitting to an adjacent blade 22 when the device 2 is in the closed configuration, as shown in FIGS. 1 and 5. Furthermore, in the centre of the inner side 30 of the blade 22, and extending parallel with the elongate axis thereof, there is provided a linear groove 26. When the device 2 is closed, the grooves 26 on each of the four blades 22 collectively create a single channel in which a guide wire (not shown) can be accommodated, and which is used by the clinician when fitting the device 2 on the patient, as will be described later.

The body 24 of each retractor 16 is slidably located into a straight guide slot 28, which is cut into the lower body 10 of the device 2, and extends radially outwardly from the centre of the body 10 to its circumferential edge, as shown in FIG. 1. Each retractor body 24 is arranged, in use, to slide along its corresponding linear guide slot 28 in either direction (i.e. towards the periphery or towards the centre of the body 10) as the device 2 is moved between the open and closed configurations.

As shown most clearly in FIG. 3, the upper body 8 of the device 2 includes four angled or non-linear "cam" guide slots 20, which extend generally outwards towards the periphery of the body 8. The radial distance of an inner end 20a of each angled guide slot 20 is less than the radial distance of the opposite outer end 20b of the slot 20. The body 24 of each retractor 16 includes a protrusion or pin 18, which extends into one of the "cam" guide slots 20, and these angled routes 20 each act as a cam mechanism, as will be described below to cause the retractors to slowly open and close as the device 2 is opened and closed.

Starting with the device in the closed configuration shown in FIG. 1, as the upper handle 12 is rotated with respect to the lower handle 14 (i.e. handles 12, 14 are urged together), each of the retractor pins 18 are urged gradually outwardly along the angled guide slots 20 towards the periphery of the body 8. Simultaneously, as the pins 18 move along their guide slots 20, each retractor 16 is urged outwardly along the straight guide slots 28, i.e. radial expansion. Thus, the upper angled guide slots 20 serve to draw the retractors 16 outwards, while the lower straight guide slots 28 ensure that the retractors 16 are moved in a lateral direction.

The length of each angled guide slot 20 is greater than the length of each straight guide slot 28 in order to provide a slow and gradual control of the motion of the retractors 16 along slots 28, thereby forming the stoma. Hence, the clinician can ensure that that the patient is not harmed by the retractors 16 radially expanded too quickly. Also, as can be seen in FIG. 3, each end 20a, 20b of the guide slots 20 is provided with a small kink or detent 38, 40, which provides friction and therefore a small amount of resistance to the position of the pin 18 when the device 2 is either in the open configuration shown in FIG. 2, or the closed configuration shown in FIG. 1. The smooth track along the slot 20 between the ends 20a, 20b ensures that the pin 18 moves gradually and smoothly therealong, as the device 2 is opened or closed. In one embodiment (not shown), the guide slots 20 can have one or more small recesses or detents into which the engagement pin 18 would slide into, and which would indicate set measurements corresponding to the size of the stoma that has been created.

As shown in FIGS. 6 and 7, the lower surface of the retractor body 22 includes a first ratchet 34 that engages with a second ratchet 36 which is provided in the base of the guide slot 28 in the lower body section 10 (see FIG. 1). Therefore, as the ratchets 34, 36 engage with each other at different positions therealong, the clinician can let go of the device 2 without the risk of the stoma inadvertently closing. The ratchets 34, 36 also collectively act as a retraction indicator by providing a means of indicating the desired diameter of the stoma created by the radially expanding blades 22, and a way of improving usability. This gives the operator feedback of the distance that has been retracted (e.g. five clicks for the correct size) or have a ratchet placed at the desired sizings. This will ensure that the operator is aware of how far the blades 22 have dilated, thus ensuring that the least amount of pressure is applied to produce the desired dilatation and so that there is no over-dilation. In one embodiment, the ratchets 34, 26 could be built into the guide slot 36 and engage with the retractors 34, or, in another embodiment, be built into the upper or lower section 4, 6 either in the bodies 8, 10 or the handles 12, 14.

Other ways of indicating dilation include a measuring guide corresponding to the movement of the upper handle 12 and the lower handle 14, or the movement of one or more of the retractor bodies 24 in relation to the upper handle 12 with the upper body 8 being at least partially transparent to show the position of the retractor body 24 therein. A measurement guide would be on the upper handle 12, which would mean that the size of stoma made will allow the operator to insert the correct size tube. The measurement guide would indicate either tracheostomy tube sizing or diameter of the stoma created.

Details of how the device 2 is used will now be described. In order to create a stoma, the clinician first makes an incision in the patient's skin at the target site (e.g. on the trachea or the chest etc) with a hypodermic needle (not shown). Insertion of the needle is carried out by fibreoptic guidance in order to locate the tracheal lumen. The needle is then removed leaving a sheath in place through which a guidewire (not shown) is inserted. The device 2 shown in the Figures is then supplied in the closed configuration with all of the blades 22 in the closed position (i.e. held together), as shown in FIG. 1. The closed blades 22 of the device 2 each have an internal groove 26 and form a channel through which the guidewire extends. The device 2 is then fed over and down the guidewire towards the patient, and the blades 22 of the device 2 then are inserted into the trachea between the cartilage rings. The handle 12, 14 of the device 2 are then rotated with respect to each other and brought together, which, as mentioned above, causes the retractor pins 18 on the retractors 16 to be gradually urged outwardly along the angled guide slots 20 towards the periphery of the body 8. As the pins 18 move along angled slots 20, each retractor 16 radially expands outwardly along the linear guide slots 28, thereby forming the stoma. Once the desired retraction position has been achieved, the operator removes the device 2 and inserts a medical tube such as a tracheostomy tube (not shown) or other tube for fluid to pass along. The tracheostomy tube could be inserted into the stoma while the device 2 is in place retracting the stoma. Some tracheostomy tubes have a folding neck flange thus allowing the device 2 to be withdrawn over the tube.

Advantages of the device 2 reside in the fact that the dilation performed by the blades 22 ensures a uniform opening of the stoma, including skin and tracheal tissue. This also reduces the risk of post-procedure complications. Another advantage is that there is no need to use blind insertion of long dilators (e.g. using the prior art the Blue Rhino device) into the trachea, which is associated with complications, such as posterior tracheal wall perforation, anterior tracheal wall damage, and cartilage ring fracture. The methods described herein also reduce the risk of posterior tracheal wall rupture since it is not necessary to apply downward pressure on the anterior tracheal wall for dilation.

The invention claimed is:

1. A stoma-creating apparatus for creating a stoma in a subject, the apparatus comprising:
    first and second members; and
    a plurality of dilation means provided on at least one of the first member and the second member, each dilation means comprising a body section and a blade extending from the body section, wherein each blade defines a single groove that extends in a substantially parallel direction with respect to the elongate axis of the blade, and wherein each blade has a distal end that is beveled to a tip,
    wherein, in use, upon respective movement of the first and second members, the stoma-creating apparatus is arranged to move between (i) a first closed configuration in which the plurality of dilation means is substantially closed, and the grooves on the blades of the body sections of the plurality of dilation means collectively create a single channel in which a guide wire can be accommodated, and the tips of the blades meet to form a single pointed end to further ease insertion into the subject, and (ii) a second open configuration in which the plurality of dilation means are substantially dilated, thereby creating a stoma in the subject.

2. The apparatus according to claim 1, wherein the apparatus is a tracheostomy apparatus.

3. The apparatus according to claim 1, wherein at least one of the first member and the second member comprises a ring-shaped body and a handle.

4. The apparatus according to claim 3, wherein the bodies of the first and second members are rotatably attached to each other such that they are capable of moving between the open and closed configurations.

5. The apparatus according to claim 4, wherein the plurality of dilation means is arranged, in use, to engage with the subject and dilate to form the stoma, as the apparatus is moved from the closed configuration into the open configuration.

6. The apparatus according to claim 4, wherein an outer side of each blade is substantially curved so as to form a cylindrical shape when adjacent blades are brought together when the apparatus is in the first configuration, and wherein an inner side of the blade is beveled to allow for a close fitting to an adjacent blade when the apparatus is in the first configuration.

7. The apparatus according to claim 1, wherein the body section of each dilation means defines a plane, and wherein the blade of each dilation means extends at an angle of between 70° and 110° with respect to the plane of the body section of the dilation means.

8. The apparatus according to claim 1, wherein the first member comprises one or more guide slots, wherein the one or more guide slots of the first member are arranged to slidably receive the plurality of dilation means, and wherein the one or more guide slots of the first member extend radially outwardly from an inner portion towards a periphery of the first member.

9. The apparatus according to claim 8, wherein the body section of each dilation means is arranged, in use, to slide along its corresponding guide slot as the apparatus is moved between the open and closed configurations.

10. The apparatus according to claim 8, wherein the second member comprises one or more guide slots, wherein the one or more guide slots of the second member are arranged to receive the plurality of dilation means.

11. The apparatus according to claim 10, wherein the one or more guide slots of the second member are arranged to receive a protrusion or pin extending out of the body section of a dilation means of the plurality of dilation means.

12. The apparatus according to claim 11, wherein the one or more guide slots of the second member extend at an angle from an inner portion towards a periphery of the second member, and wherein the one or more guide slots of the second member are non-linear.

13. The apparatus according to claim 11, wherein the radial distance of an inner end of the one or more guide slots of the second member is less than the radial distance of the opposite outer end of the one or more guide slots of the second member.

14. The apparatus according to claim 11, wherein each pin is arranged, in use, to slide along its corresponding guide slot of the first and second members as the apparatus is moved between the open and closed configurations.

15. The apparatus according to claim 11, wherein, in use, the apparatus is arranged to be moved from the first configuration to the second configuration, and urge each pin along its corresponding guide slot of the second member towards the periphery of the second member, wherein, as each pin moves along its corresponding guide slot of the first member, the apparatus is arranged, in use, to urge each dilation means along the guide slot of the first member towards the periphery of the first member.

16. The apparatus according to claim 11, wherein the plurality of dilation means radially expand as they are moved towards the second configuration, and wherein the one or more guide slots in the second member are longer than the one or more guide slots in the first member.

17. The apparatus according to claim 11, wherein each guide slot provided in the second member comprises one or more detents for receiving the pin.

18. The apparatus according to claim 8, wherein the apparatus comprises dilation indication means for indicating to an operator the desired diameter of the stoma that has been created, wherein the indication means comprises a ratchet provided in a guide slot in the first member and a corresponding ratchet provided on a dilation means of the plurality of dilation means.

19. The apparatus according to claim 1, wherein the body section of each dilation means defines a plane, and wherein the blade of each dilation means extends at an angle of between 80° and 100° with respect to the plane of the body section of the dilation means.

20. The apparatus according to claim 1, wherein the body section of each dilation means defines a plane, and wherein the blade of each dilation means extends at an angle of between 85° and 95° with respect to the plane of the body section of the dilation means.

* * * * *